United States Patent
Albu-Schäffer et al.

(10) Patent No.: US 7,646,161 B2
(45) Date of Patent: Jan. 12, 2010

(54) METHOD FOR CONTROLLING A ROBOT ARM, AND ROBOT FOR IMPLEMENTING THE METHOD

(75) Inventors: Alin Albu-Schäffer, Munich (DE); Christian Ott, Munich (DE); Ulrich Hagn, Pahl (DE); Tobias Ortmaier, Germering (DE)

(73) Assignees: Deutsches Zentrum Fuer Luft-Und Raumfahrt E.V., Cologne (DE); Brainlab AG, Feldkirchen (DE)

( * ) Notice: Subject to any disclaimer, the term of this patent is extended or adjusted under 35 U.S.C. 154(b) by 246 days.

(21) Appl. No.: 11/600,959

(22) Filed: Nov. 15, 2006

(65) Prior Publication Data

US 2007/0120512 A1    May 31, 2007

(30) Foreign Application Priority Data

Nov. 16, 2005 (DE) .................. 10 2005 054 575

(51) Int. Cl.
*G05B 19/4061* (2006.01)
*G05B 19/33* (2006.01)

(52) U.S. Cl. ............... 318/568.2; 700/245; 700/248; 700/261; 901/30; 901/41; 248/282.1; 248/274.1; 248/276.1; 248/278.1

(58) Field of Classification Search ............ 318/568.2, 318/568.21; 700/245, 249, 254, 259, 248; 700/261; 901/1, 30, 41; 248/282.1, 274.1, 248/276.1, 278.1
See application file for complete search history.

(56) References Cited

U.S. PATENT DOCUMENTS

| | | | | |
|---|---|---|---|---|
| 4,925,312 A | * | 5/1990 | Onaga et al. ............... | 700/261 |
| 5,784,542 A | * | 7/1998 | Ohm et al. ................. | 700/260 |
| 5,855,553 A | * | 1/1999 | Tajima et al. .............. | 600/407 |
| 6,459,926 B1 | * | 10/2002 | Nowlin et al. .............. | 600/429 |
| 6,659,939 B2 | * | 12/2003 | Moll et al. ................. | 600/102 |
| 7,390,325 B2 | * | 6/2008 | Wang et al. ................ | 606/10 |
| 7,411,576 B2 | * | 8/2008 | Massie et al. .............. | 345/156 |
| 7,413,565 B2 | * | 8/2008 | Wang et al. ................ | 606/1 |
| 7,445,594 B1 | * | 11/2008 | Borst et al. ................ | 600/37 |
| 2004/0176875 A1 | * | 9/2004 | Iribe et al. ................. | 700/245 |
| 2007/0013336 A1 | * | 1/2007 | Nowlin et al. ........... | 318/568.21 |

OTHER PUBLICATIONS

Alin Albu-Schäffer et al; Cartesian Impedance Control Techniques for Torque Controlled Light-Weight Robots; EEE International Conference on Robots and Automation, Washington, DC; pp. 657-663, 2002.

* cited by examiner

*Primary Examiner*—Rita Leykin
(74) *Attorney, Agent, or Firm*—Clements Bernard, PLLC; Gregory N. Clements

(57) ABSTRACT

In a method for controlling a robot arm, which is particularly suitable for use in medical applications, a robot arm (10) with a redundant number of joints is used. A torque acting in at least one joint (12a, 12b) is sensed. By means of a control device, the torque acting in this joint (12a, 12b) is controlled to become substantially 0.

13 Claims, 5 Drawing Sheets

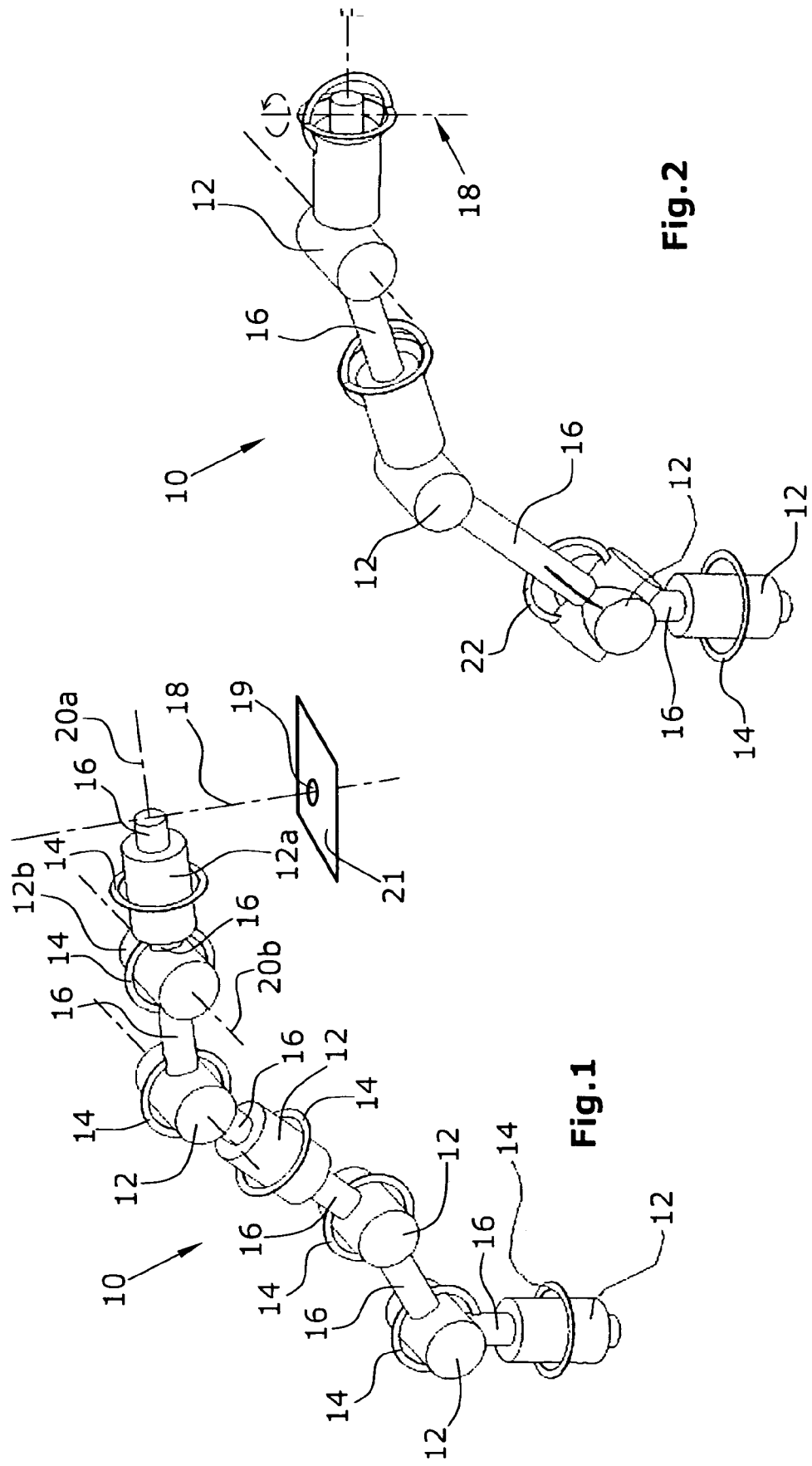

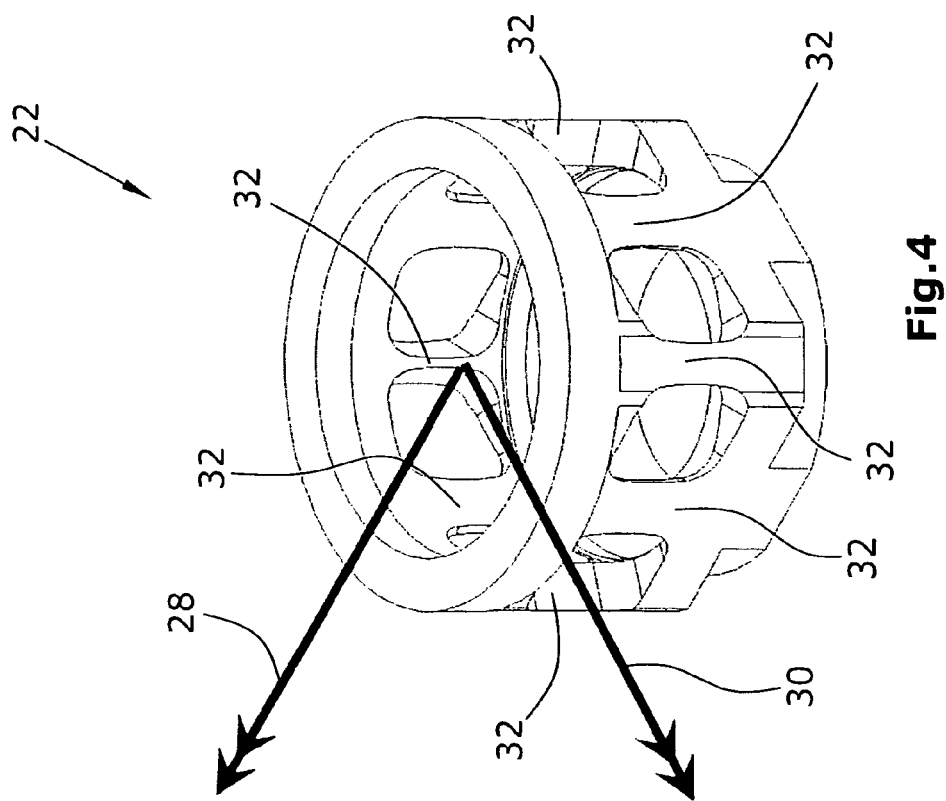
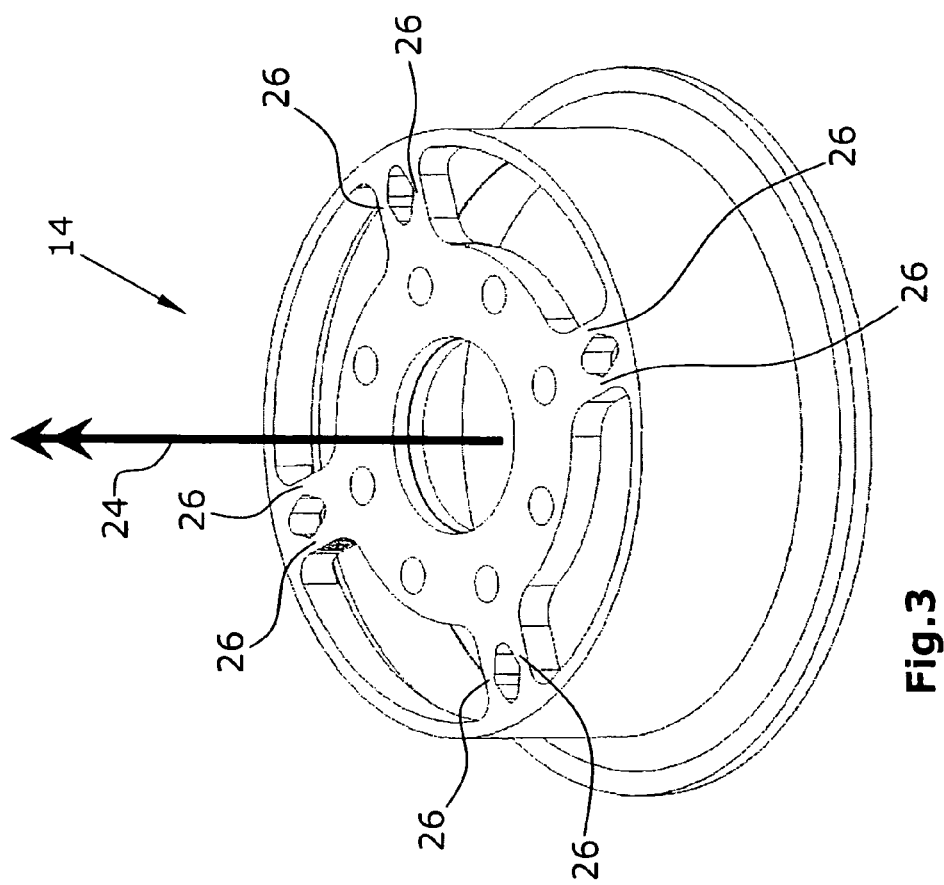

ns and/or the forces acting on openings. Further, it is an object of the invention to provide a device for practicing the method.

METHOD FOR CONTROLLING A ROBOT ARM, AND ROBOT FOR IMPLEMENTING THE METHOD

BACKGROUND OF THE INVENTION

The present application claims the priority of German Patent Application No. 10 2005 054 575.0-15 which is herewith incorporated herein by reference.

FIELD OF THE INVENTION

The invention refers to a method for controlling a robot arm which is particularly suitable for use in medical applications. Further, the invention refers to a robot for implementing the method.

DESCRIPTION OF RELATED ART

With robots intended to interact with a dynamic environment, if a suitable modelling of the environment is impossible or can be achieved only with great efforts, mere position control or mere force control will yield only unsatisfactory results in view of avoiding collisions. A predictive modelling of an environment is very hard to realize, especially in medical applications.

The events occurring during medical procedures, which are not or only very vaguely predictable, and the lack of space prevailing there lead to a high probability of collision in the use of medical robots. On the one hand, no preoperative planning that would be sufficiently detailed and flexible corresponding to the actual events can be performed to avoid collisions, and on the other hand, the close interaction of the robot with the patient and a practitioner makes it impossible to define necessary safety areas (workcell) as is done in industrial robotics. As a result, the risk of collisions has to be assessed during the operation of the robot and has to be avoided using corresponding methods. With a fixed robot base and a robot end effector in engagement which is thus also partly or completely fixed, an impending collision of the elbow of a robot, for example, with another fixed object can only be avoided by stopping the robot. An evasion by the elbow, while the robot end effector maintains its position and orientation, is not possible.

For example, when robots are used in minimally invasive medical applications, a robot arm guides thin, long instruments that are introduced through small natural or artificial openings in a patient's body. It has to be ensured that the contact forces tangential to the patient surface are minimized at the opening site to avoid lesions at the openings. Since the opening site varies with respect to the Robot due to breathing and movements by the patient, a functionality is required that allows to minimize the forces described regardless of and without knowledge of the position of the opening site.

A corresponding problem also exists in other applications, for example in industrial applications, in which a robot is used in limited spaces and/or sensitive components and the like are present in the vicinity of the robot. The above described problem exists especially if an instrument, such as a tool, a camera or the like, carried by a robot arm is passed through an opening into a device such as a turbine. This opening is technically equivalent to an opening in a patient and has to be considered in the control.

SUMMARY OF THE INVENTION

It is an object of the present invention to provide a method for controlling a robot arm which reduces the risk of colli- The object is achieved, according to the invention, with a method according to claim 1 and a device of claim 13, respectively.

In the present method for controlling a robot arm, a robot arm with a redundant number of joints is used. The individual joints are usually interconnected through connecting elements. The robot arm is moved through actuators, such as transmissions and adjusting elements, which are connected with the joints and/or the connecting elements. A torque sensor detects an external torque acting in at least one joint. To achieve this, a torque sensor may be arranged in the joint itself and/or be provided at a connecting element connected to the joint. The torque acting in the at least one joint is detected and supplied to a control means. The control means serves to drive the actuators of the robot arm, such as the transmissions, the adjusting elements and the like, such that the external torque is controlled to become substantially zero on at least this one joint. In doing so, preferably, the moments caused by gravitation are considered, particularly calculated on the basis of a model and subtracted from the measured total moment. As provided by the invention, this is an active control of the robot arm within an space critical in terms of collisions and the like, which space is especially an opening in a device or an opening in a patient, wherein the forces acting on the opening are reduced according to the invention.

The three common methods which, in contrast to a position or force control, allow for a control of the dynamic behaviour in Cartesian coordinates are impedance control, admittance control, and impedance projection.

Impedance control is based on an existing torque control on the level of the joints. The deviation of the robot position from a defined set position is measured and a desired generalized force (forces and moments) is determined corresponding to the desired dynamic behaviour. This force is mapped to corresponding joint torques through the known kinematic of the robot. Eventually, the torques are set via the subordinate torque control.

Contrary to the impedance control, admittance control is based on an existing position control of the robot on the level of the joints. Here, the generalized forces acting on the robot from outside have to be measured. Starting from these forces, a movement of the robot is determined that corresponds to the desired dynamic behaviour of the robot and is commanded to the robot via an inverse kinematic and the subordinate position control.

The so-called impedance projection is another method suited to obtain a desired dynamic behaviour. Here, it is assumed that it is possible to control the joint impedance, i.e. the dynamic behaviour of the robot in joint coordinates. In contrast to the impedance and admittance controls, wherein forces and positions are mapped to the respective values in joint coordinates, the impedance projection provides for a projection of the various parameters that describe the desired behaviour in Cartesian coordinates onto the respective parameters in the joint coordinates.

The above described methods are described in particular in "Cartesian Impedance Control Techniques for Torque Controlled Light-Weight Robots", Alin Albu-Schäffer et al., IEEE International Conference on Robots and Automation, Washington D.C., pp. 657 to 663, 2002, the impedance control being referred to as "stiffness control" in this document.

Obtaining a desired Cartesian behaviour may be achieved based on a subordinate position, torque or joint impedance control. According to the invention, realizing these controls is facilitated preferably by integrating moment sensors in the joints of the robot. The sensor detects the one-dimensional torque acting at the output of the transmission. This value may then be used in controlling as a measured value and thus the elasticity of the joints can be taken into account in the control.

In particular, torque sensors, in contrast to the use of a force moment sensor at the end effector, also measure those forces that do not act on the robot end effector but on the segments of the robot, such as the connecting elements. This implies that it is of no importance whether the robot is guided manually at its end effector flange or another optional point (e.g., the elbow), the manual guiding of the robot arm being allowed by a completely flexible control (based on the above control methods). Moreover, the above described control methods allow to realize different impedances/admittances with various degrees of freedom (in the joint angle space or the Cartesian space) independent of each other, but also dependent on the spatial arrangement of the robot. This makes possible a haptic exchange of information between the robot and the operator and will be described in detail in the following with reference to examples of application:

Flow of information: robot->operator:

By means of control methods outlined above, any desired information can be haptically reproduced with the robot. For example, it is possible to flexibly control the robot along a determined trajectory, yet to control it rigidly in all other directions. In this case, the robot may again be moved under manual guiding, however, only along the defined trajectory, the robot not allowing any other movement. The robot thus provides haptic feedback to the operator regarding trajectories to follow. Thereby, in pre-operative planning, critical areas of movement can be blocked (e.g., to avoid lesions to vital organs or blood vessels). Thus, the robot supplies the practitioner with a feedback about the reliability of the movement performed.

Flow of information: operator->robot:

Further, the operator can command robot movements by impressing forces on the robot arm (haptic interaction). This possibility of interacting with the entire robot arm by manual guiding, based in this case on the control methods outlined above (this type of interaction is also referred to as soft robotics), is an important approach to the Implementation of robots, especially in environments difficult to predict: in particular, it allows for the use of robots in medical applications, since avoiding collisions by a preoperative planning of trajectories is not always practicable because of the dynamic and hardly predictable scenario at the operating table. If, for example, a collision between the robot and the environment is imminent, the robot may be given a collision-free configuration also by a non-specialist (e.g., a surgical nurse) using the above described methods, without having to interrupt the surgical procedure. In this sense, the above described operating method is ideal for the use of robots in medical applications.

It is particularly preferred to correspondingly control two joints such that the torque acting on two joints is controlled to substantially zero. Preferably, these are two adjacent joints connected through a connecting element, e.g., a web-shaped component or the like. In particular, the joints controlled according to the invention are two joints that are closest to an environment element on which no forces are exerted, and which can generate forces in the tangential plane at the penetration point. In minimally invasive applications in medikine, the present invention thus considerably reduces the occurrence of forces at the opening in the patient, with no significant forces occurring anymore because of the control, so that preferably no damages occur at the opening site. The joints controlled according to the invention are joints whose torques would generate a bearing force of the instrument at the penetration point of the inner edge of the opening in the patient.

The control is preferably effected within predetermined limit values.

The present invention thus allows to maintain both the base and the end effector of the robot arm at a fixed position and a fixed orientation, by using a robot arm with a redundant number of joints, i.e. redundant kinematics. Here, the base of the robot arm is a first, possibly stationary, element of the robot arm. The end effector is the last member of the robot arm, e.g., supporting the robot hand, a medical device etc. At the same time, the present method allows to move an end effector with a fixed position and orientation through different arm configurations, i.e., to perform a zero space movement. It is thus possible to perform certain end effector movements with a kinematically redundant robot or a robot with redundant joints, which movements may be, for example, movements to be performed during a surgical operation, while an elbow of the robot arm is moved to other positions to avoid collisions.

In a particularly preferred embodiment of the invention, the robot arm guiding an instrument is made to adopt one of a plurality of configurations in which the joint axes of the two torque controlled joints, in particular, are vertical to each other. In a particularly preferred configuration, the instrument axis is vertical to the two joint axes. However, a zero force control in the plane can always be obtained well if the instrument axis is not vertical to the two joint axes, but includes an angle other than zero with the two joint axes. Preferably the control is effected by zero moment control which may be considered a special type of impedance control (the interaction torques occurring are substantially zero). Because of the zero moment control in those two joint axes, the robot can generate no substantial translational forces at the opening site that are parallel to the plane spanned by the two joint axes, regardless of the location of the opening site. By sliding the instrument along the instrument axis, no substantial forces are thus generated in the plane tangential to the penetration point. Technically, in zero point control, the interaction torque acting in the joint is detected and controlled to become 0 by the drive. Due to interfering influences, such as the inertia of the components between both joints and the opening site, and due to friction, forces may occur at the opening site. By considering these values in a model, corresponding correction terms can be included in the zero moment control of both joints, whereby the forces to be avoided can be minimized. These terms may include the acceleration forces, the centrifugal forces, Coriolis forces or, for example, friction forces.

In contrast to the use of passive joints (free movement), the described present method offers the possibility to switch to an operating mode that allows for a controlled movement of the robot when the instrument is pulled from the opening and the patient's body (extracorporeal mode). In a robot with passive joints, these would not be controllable when the instrument is no longer within the patient (intracorporeal mode), so that the robot cannot be used in this situation. Only by the described possibility to switch between the intracorporeal and the extracorporeal modes is it possible, for example, to have the robot arm change the instrument automatically. Switching to free movement can be effected based on software. Besides, such a robot may also used in purely extracorporeal applications.

Therefore, the present method for controlling a robot arm offers the following advantages:

- haptic interaction with robot arms, based on impedance/admittance control or impedance projection, to manually position the robot arm with a simultaneous haptic feedback.
- online collision avoiding for robots in medical applications by a redundant number of joints, without interruption of the end effector movements to be performed.
- zero moment control of at least two robot joints in the manipulation of laparoscopic instruments to reduce the transmission of translational forces vertical to the instrument axis at the trocar point in minimally invasive surgery.

Preferably, a tactile sensor is provided at the instrument shaft. The tactile forces sensed by the sensor can be taken into consideration in the control. These are forces acting on the instrument tangential to the plane of the patient. These forces, preferably taken into account in the control, can be considered in addition to or instead of the moments measured in the robot axes or robot joints.

Preferably, a redundant number of joints is provided. Thus, the position of one or a plurality of connecting elements can be altered through haptic interaction, the position of the end effector remaining unchanged. Here, furthermore, no substantial forces act on the penetration point. It is particularly preferred to use the redundancy for optimizing or enhancing a quality criterion. This is done especially to orientate the two zero moment controlled axes substantially vertical to the instrument axis.

The invention further relates to a robot which is especially suitable for practicing the above described method. Such a robot has a robot arm with a plurality of joints, the number of joints being redundant. In this context, redundant means that the robot arm has a higher number of degrees of freedom than would be necessary for a manipulation in the corresponding working space. Connecting elements are provided between the individual joints, in particular web-shaped arm parts and the like. Further, the robot arm has an end effector carrying, for example, the robot hand, is connected to a medical instrument, etc. The joints and/or the connecting elements are connected with actuators, such as transmissions, servomotors, etc., for moving the robot arm. Further, torque sensors are provided. These may be torque sensors that are integrated in the joints and/or connected with the connector elements. Moreover, the robot includes a control device connected to the torque sensors and the actuators. By a corresponding processing of the signals transmitted from the torque sensors to the control device, the actuators are driven to execute the above described method of the present invention.

The robot is configured preferably as described with respect to the present method.

In particular, the invention refers to the use of a robot in practicing the present method.

BRIEF DESCRIPTION OF THE DRAWINGS

The following is a detailed description of the invention by means of a preferred embodiment and with reference to the accompanying drawings.

In the Figures:

FIG. 1 is a schematic general illustration of a robot arm according to a first embodiment of a robot arm, FIG. 2 is a schematic general illustration of a robot arm according to a second embodiment of a robot arm, FIG. 3 is a schematic perspective view of a single axis torque sensor adapted to be used in a robot arm illustrated in FIG. 1, FIG. 4 is a schematic perspective view of a multi-axis torque sensor adapted for use in a robot arm illustrated in FIG. 2, and FIGS. 5-7 show examples of flow charts for zero moment controls according to the invention, based on impedance control, admittance control and impedance projection.

DESCRIPTION OF PREFERRED EMBODIMENTS OF THE INVENTION

Figure 5:
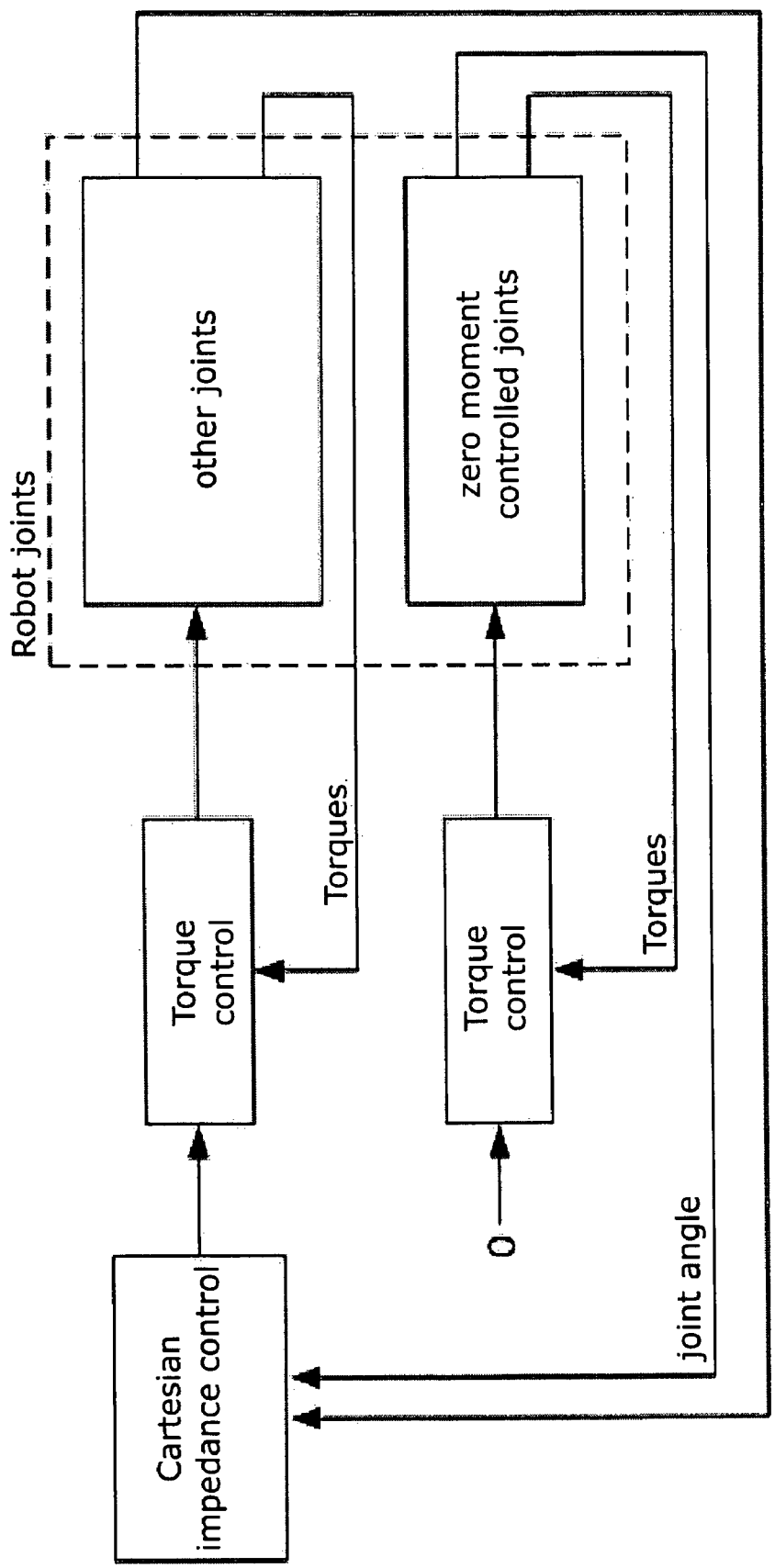

A robot arm 10 comprises a plurality of joints 12 which, in a first embodiment (FIG. 1), each include a torque sensor 14 arranged coaxial to the joint. The torque sensor 14 is a torque sensor integrated in the joint. In the embodiment shown, rod-shaped connecting elements 16 are provided between the individual joints. An end effector (not illustrated), such as a robot hand or the like, is connected to the last or free connecting element 16. In the embodiment illustrated, an instrument axis 18 extends vertical to the last rod-shaped connection element 16.

In the embodiment represented, the joints 12a and 12b are, for example, the two joints essential for practicing of the present method. The joint axes 20a, 20b of both joints 12a, 12b extend vertical to each other and to the instrument axis 18. According to the invention, the actuators that move both joints 12a, 12b are driven by a control device (not illustrated) such that the interaction torques in the two joints 12a, 12b are substantially zero. Suitable adjusting elements and/or transmissions may be provided as the actuators. The measuring results of the torque sensors 14 are also supplied to the control device to be in a position to perform a corresponding control according to the present invention.

In a second embodiment (FIG. 2), identical or similar components are identified by the same reference numerals. As an alternative to a torque sensor 14 arranged coaxial with a joint 12, a torque sensor 22 may be provided that is connected with the adjacent connecting element 16. However, transverse forces that may have to be taken into account can occur thereby, which forces would have to be eliminated by correction terms or have to be considered in the control, for example. The torque sensor 22 connected with an adjacent connecting element 16 is advantageous in that a plurality of joints can be comprised or monitored in common by one sensor. Possibly, a combination of both sensor types or sensor arrangements may be particularly advantageous. Both types of torque sensors represented in FIG. 1 and FIG. 2 are advantageous over known six-axes force moment sensors arranged at the tip or the free end of the robot arm in that forces of the connecting elements can also be detected. This allows for a correct implementation of kinematically redundant robot arms with more than six degrees of freedom.

An example of a sensor 14 adapted to be integrated in a joint is illustrated in FIG. 3. Here, the torque to be measured, illustrated by the arrow 24, is detected through the deformation of the measuring points 26.

A multi-axis sensor that could be implemented as the sensor 22 in the embodiment of FIG. 2 is illustrated in FIG. 4. Such a sensor detects the torques 28, 30 as well as transverse forces through deformations at the measuring points 32.

Figure 6:
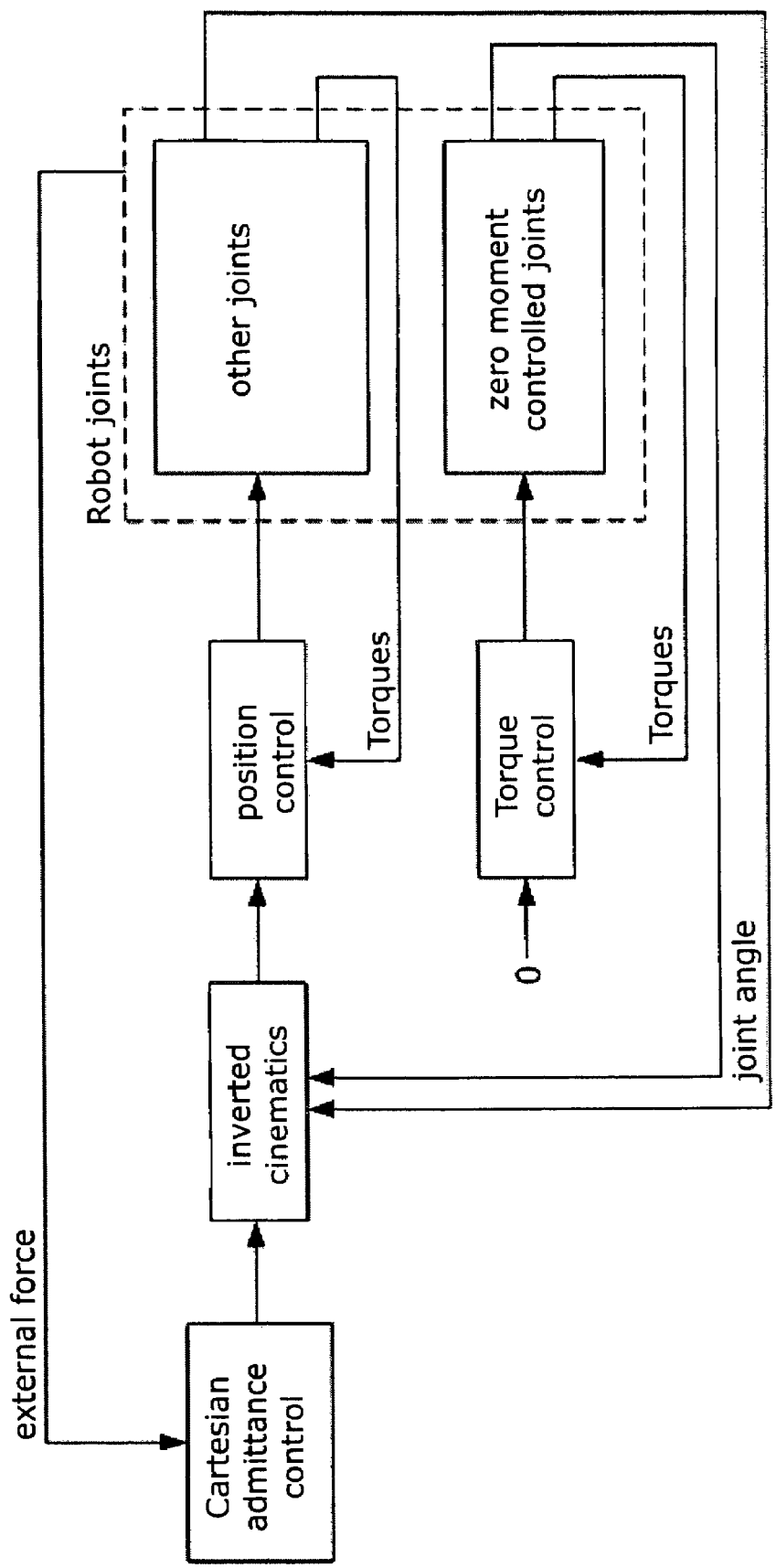
Figure 7:
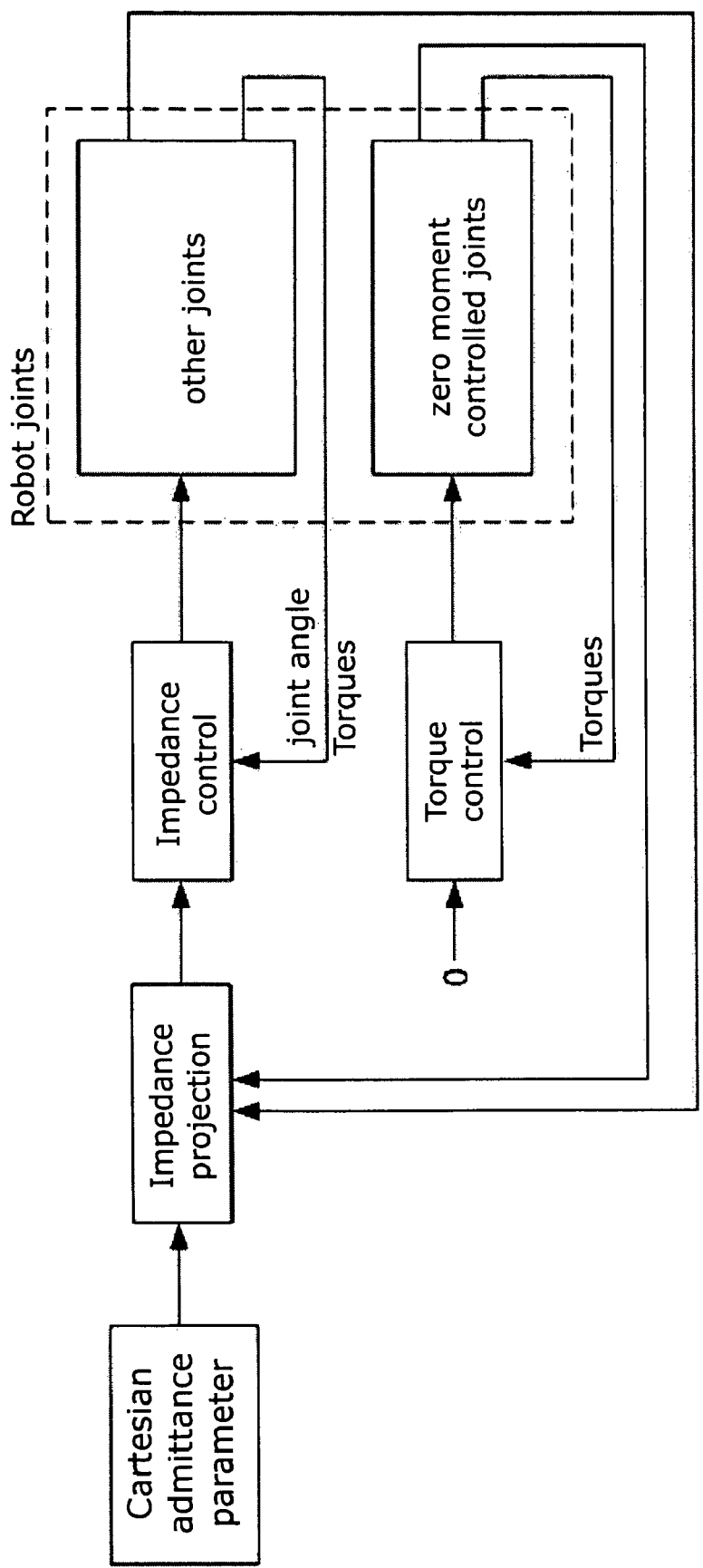

The following is an explanation of a preferred embodiment of different control methods with reference to FIGS. 5 to 7.

Impedance control (FIG. 5) uses a subordinate torque control of the individual joints. This is made possible in particular by measuring the moments on output side. A value of 0 Nm is used as the set torque for the zero torque controlled joints 20a and 20b of FIG. 1 so as to prevent the exertion of forces on the opening in the patient surface. The other joints receive their set torque from a superordinate impedance control rule. The implementation of this external control circuit requires the measuring of all joint positions.

Admittance control (FIG. 6) is based on a subordinate position or speed control of the joints not zero moment controlled. In an external control circuit, an admittance control rule is used that requires the measured generalized forces as its input value. The combination with the subordinate position or speed control is effected through inverted kinematics. To this end, the joint angles of all joints have to be measured.

Impedance projection (FIG. 7) uses a joint impedance control of the joints not zero moment controlled. The implementation of the projection requires the measuring of all joint angles.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

What is claimed is:

1. A method for controlling a robot arm for use in medical or industrial applications, wherein
   a robot arm (10) with a redundant number of joints is used wherein at least a first and a second joint (12a, 12b) are controlled and wherein the redundancy of joints is used to optimize a quality criterion, to align two zero moment controlled axes substantially vertical to the instrument axis,
   an instrument connected to said robot arm is passed through an opening (19),
   a torque acting in at least one joint (12) is detected,
   the interaction torque acting in said joint (12) is controlled to substantially zero by means of a control device in order to reduce the forces acting on the edge of the opening,
   the control of at least a first joint (12a), which due to its position in space can generate a force in the plane parallel to the patient, is performed such that the force is substantially zero at the patient penetration point, and
   joint axes (20a, 20b) of said first and second joints are vertical to each other, and the instrument axis (18) vertical to both joint axes (20a, 20b) and includes an angle other than zero with the joint axes.

2. The method of claim 1, wherein the control using the control device is performed when predetermined limit values are exceeded or under-run.

3. The method of claim 1, wherein the control is effected using a zero moment control.

4. The method of claim 1, wherein the joints (12a, 12b) connected with a joint connecting element (16) that is closest to the element of the environment are controlled.

5. The method claim 1, wherein correction terms are included in the control to compensate for moments and/or forces caused by inertia and/or friction.

6. The method of claim 1, wherein the control of the robot arm is supported by a haptic flow of information.

7. The method of claim 1, wherein at least one of the joints controlled is adapted to be switched to a controlled free movement.

8. The method of claim 1, wherein, due to the redundant number of joints, a change of position of at least one connecting element (16) is possible through haptic interaction without changing the position of the end effector, the forces acting on the edge of the opening being substantially zero.

9. The method of claim 1, wherein the optimized quality criterion is alignment of the two zero moment controlled axes substantially vertical to the instrument axis.

10. A robot, for use in medical applications, comprising
    a robot arm (10) with a plurality of joints (12), the number of joints being redundant, connecting elements (16) being arranged between the joints (12), an end effector, and actuators and torque sensors (14, 22) connected with the joints (12) and/or the connecting elements (15), wherein a first and a second joint (12a, 12b) are connected with a connecting element (16) and the first and second joints (12a, 12b) are arranged closest to an element of the environment and
    a control device, connected with the torque sensors (14, 22) and the actuators, for executing the method of claim 1 wherein said first joint (12a), a joint closest to the element of the environment, includes a torque sensor (14, 22) wherein the torque sensor is an internal torque sensor (14) integrated in the joint and/or a torque sensor (22) connected with the adjacent connecting element (16).

11. The method of claim 3 wherein the control is effected using an impedance control.

12. The method of claim 3 wherein the control is effected using an admittance control.

13. The method of claim 3 wherein the control is effected using an impedance projection.

* * * * *